United States Patent [19]

Gregoire et al.

[11] Patent Number: 5,449,510
[45] Date of Patent: Sep. 12, 1995

[54] EMULSION OF THE OIL-IN-WATER TYPE BASED ON SILICONE OIL AND ITS USE IN COSMETICS AND DERMATOLOGY

[75] Inventors: Nathalie Gregoire, Sceaux; Anne Boelle, Meudon, both of France

[73] Assignee: L'Oreal, Paris, France

[21] Appl. No.: 93,582

[22] Filed: Jul. 19, 1993

Related U.S. Application Data

[63] Continuation of Ser. No. 888,596, May 27, 1992, abandoned.

[30] Foreign Application Priority Data

May 27, 1991 [FR] France .................. 91 06345

[51] Int. Cl.$^6$ ................................. A61K 7/00
[52] U.S. Cl. ........................................ 424/60
[58] Field of Search ............................ 424/60

[56] References Cited

U.S. PATENT DOCUMENTS 4,788,001 11/1988 Narula .
4,917,891 4/1990 Kaufmann et al. .

FOREIGN PATENT DOCUMENTS

| | | |
|---|---|---|
| 0076146 | 4/1983 | European Pat. Off. . |
| 0152953 | 8/1985 | European Pat. Off. . |
| 0154837 | 9/1985 | European Pat. Off. . |
| 0200916 | 11/1986 | European Pat. Off. . |
| 0291683 | 11/1988 | European Pat. Off. . |
| 0461593 | 12/1991 | European Pat. Off. . |
| 2485923 | 1/1982 | France . |
| 2079300 | 1/1982 | United Kingdom . |
| 2206048 | 12/1988 | United Kingdom . |

OTHER PUBLICATIONS

Derwent Abstract AN-82-03953E/03 (1982).

*Primary Examiner*—James H. Reamer
*Assistant Examiner*—Michael B. Hydorn
*Attorney, Agent, or Firm*—Oliff & Berridge

[57] ABSTRACT

A stable cosmetic emulsion of the oil-in-water type contains an aqueous phase, an oily phase, and an emulsifier, with the oily phase containing at least one silicone oil and the emulsifier being a polyoxyethylenated polyorganosiloxane with the following formula:

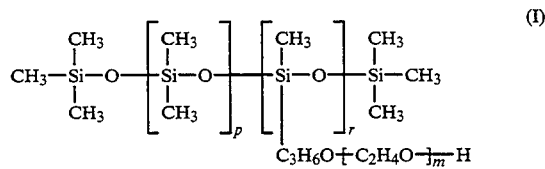

The stable emulsion is especially desirable in the fields of cosmetics and dermatology, particularly in creams, lotions, and makeup products.

20 Claims, No Drawings

EMULSION OF THE OIL-IN-WATER TYPE BASED ON SILICONE OIL AND ITS USE IN COSMETICS AND DERMATOLOGY

This is a Continuation of application Ser. No. 07/888,596 filed May 27, 1992, now abandoned.

The subject of the present invention is a stable emulsion of the oil-in-water type based on silicone oil and its use in the cosmetic and dermatological fields, particularly in creams, lotions, or in makeup products such as mascaras, makeup bases, and eye liners.

BACKGROUND OF THE INVENTION

Silicone oils are ingredients that are particularly sought after in cosmetics because they impart excellent lubricating and waterproofing properties.

Moreover, by comparison with classical oils, silicone oils form a protective film over the skin, protecting it from dehydration with no greasy effect being observed.

Until now, studies performed have not allowed appreciable proportions of silicone oils to be incorporated satisfactorily into emulsions of the oil-in-water type. Incorporation of silicone oils is limited to approximately 15% maximum and the silicone oils employed are cyclic volatile silicone oils and polydimethylsiloxanes (linear silicones) with a low viscosity (<100 centistokes).

Other studies have been performed with a view to obtaining emulsions of the oil-in-water type based on silicone oils using various surfactants, particularly nonionic and ionic surfactants. Such silicone oil-based, oil-in-water emulsions are described in U.S. Pat. No. 4,917,891, French Patent No. 2,485,923, European Patent EP 76,146, and U.S. Pat. 4,788,001.

It has been shown by these patents, however, that the use of classical surfactants does not always produce good emulsification of the silicone oils in the water.

SUMMARY OF THE INVENTION

According to the invention, it is possible to obtain emulsions of the oil-in-water type by using an emulsifier of the polyoxyalkylenated polyorganosiloxane type that has the specific and desirable characteristics of being dispersible in water and insoluble in the silicone oil-based oil phase. Thus, after a substantial research effort, it has now been found, surprisingly and unexpectedly, that it is entirely possible to obtain such stable silicone oil-based emulsions of the oil-in-water type.

An object of the present invention is a stable cosmetic or dermatological emulsion of the oil-in-water type based on silicone oil comprising an aqueous phase, an oily phase, and an emulsifier. The oily phase comprises at least one silicone oil and the emulsifier is a polyoxyethylenated polyorganosiloxane with the following formula:

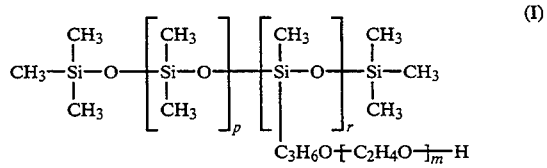

(I)

wherein:
p is a number between 15 and 35, preferably between 20 and 30,
r is a number between 2 and 6,
m is a number between 5 and 15, preferably between 8 and 12,
and p, r, and m are such that the molecular weight ratio between the polyoxyethylenated side chain and the polysiloxane chain is approximately 50:50.

DETAILED DESCRIPTION OF PREFERRED EMBODIMENTS

According to the invention, the polyoxyethylenated polyorganosiloxane with formula (I) should preferably have a hydrophilic lipophilic balance (HLB) of between 9 and 12 and a molecular weight of between 2000 and 7000, preferably between 3500 and 4500.

According to one preferred embodiment of the invention, the polyoxyethylenated polyorganosiloxane is a polyoxyethylenated polydimethylsiloxane with a molecular weight of 4000 and an HLB of 10, with a molecular weight ratio between the polyoxyethylenated side chain and the polyorganosiloxane chain of 50:50.

A number of comparative studies have been conducted and have shown the importance of the characteristics of the emulsifier with formula (I) for obtaining stable emulsions.

According to the invention, the proportion of emulsifier with formula (I) is generally between 1 and 10 wt. %, and preferably between 4 and 6 wt. %, relative to the total weight of the emulsion.

The aqueous phase of the emulsion represents 50 to 75 wt. %, and preferably 60 to 70 wt. %, relative to the total weight of the emulsion.

The oily phase of the emulsion represents 20 to 50 wt. %, and preferably 30 to 40 wt. %, relative to the total weight of the emulsion.

In this oily phase, the proportion of silicone oil is greater than 50%, and is preferably between 70 and 100 wt. %.

An emulsion according to the invention can also contain 0.05 to 20 wt. % of an agent that gels the aqueous phase.

Examples of suitable gelling agents include cellulose derivatives, polysaccharides, and acrylic polymers such as a Carbomer or a glyceryl polyacrylate.

According to the invention, the gelling agent further improves the stability of the emulsion.

As stated above, the oily phase of the emulsion comprises a silicone oil which may be a cyclic volatile silicone oil or a low-viscosity polydimethylsiloxane. Examples of suitable volatile silicone oils include cyclopentadimethylsiloxane and cyclotetradimethylsiloxane.

When the oily phase does not totally consist of a silicone oil, it may also contain plant, animal, mineral, or synthetic oils.

Examples of suitable plant oils include jojoba oil, olive oil, sweet almond oil, avocado oil, coconut oil, wheat germ oil, corn oil, palm oil, sesame oil, soy oil, argan oil, oenothera oil, borage oil, and the essential oils may be cited.

Of the animal oils, fish oil is of particular use.

Examples of suitable mineral oils include vaseline oil and isohexadecane.

Examples of suitable synthetic oils include ethyl and isopropyl palmitates, 2-ethylhexyl palmitate, alkyl myristates such as isopropyl, butyl, and cetyl myristate, hexyl stearate, octanoic and decanoic acid triglycerides, cetyl ricinoleate, and stearyl octanoate.

The oily phase may also contain dyes, sun filters, antioxidants, preservatives, and lipophilic active elements.

The aqueous phase of the emulsion may also contain, in addition to the gelling agent, water-soluble derivatives, particularly dyes, preservatives, water-soluble surfactants and moisturizers such as glycerin.

The emulsion according to the invention may also contain fragrances, essential oils, pigments, excipients, vitamins, and various other active substances for cosmetic or dermatological purposes.

The emulsions according to the invention are prepared by dispersing the surfactant with formula (I) in water and slowly adding the oily phase to this aqueous dispersion with vigorous agitation. When the emulsion contains a gelling agent, this is added, depending on its nature, either before the addition of the oily phase or after formation of the emulsion.

The emulsions according to the invention can be used in cosmetics and dermatology for face creams, body creams, or scalp and hair creams, for cleansing lotions, or body or hair lotions. These emulsions can also be used in makeup products after the addition of pigments such as in mascaras, bases, and eye liners.

Several examples of oil-in-water emulsions according to the invention will now be given for illustration but are not limiting in nature.

EXAMPLE 1

Gelled Face Cream in the Form of Oil-In-Water Emulsion

| | |
|---|---|
| Polyoxyethylenated polydimethylsiloxane with formula (I) (MW 4000 and HLB 10) | 5% |
| "Pemulen TR2" sold by the Goodrich Company | 0.1% |
| Triethanolamine | 0.1% |
| Cyclopentadimethylsiloxane | 25% |
| Jojoba oil | 10% |
| Water | 100% |

When this cream is spread on the skin it penetrates well; it is gentle and very refreshing.

EXAMPLE 2

Body Lotion in the Form of an Oil-In-Water Emulsion

| | |
|---|---|
| Polyoxyethylenated polydimethylsiloxane with formula (I) (MW 4000, HLB 10) | 4% |
| Glucose-mannose-glucuronic-acid polysaccharide (Keltrol from the Kelco Company) | 1% |
| Cyclopentadimethylsiloxane | 30% |
| Water | 100% |

This body lotion is very refreshing when applied.

EXAMPLE 3

Makeup Base in the Form of an Oil-In-Water Emulsion

| | |
|---|---|
| Polyoxyethylenated polydimethylsiloxane with formula (1) (MW 4000 and HLB 10) | 4.80% |
| Glyceryl polyacrylate gel in water (50:50) | 4.50% |
| Xanthan gum | 0.20% |
| Cyclopentadimethylsiloxane | 22.60% |
| Jojoba oil | 9.00% |
| Yellow iron oxide | 0.95% |
| Brown and yellow iron oxides | 0.35% |
| Black iron oxide | 0.15% |
| Titanium oxide | 3.25% |
| Methylparaben | 0.20% |
| Water | 100% |

This base is easily applied, gives a natural effect, and is refreshing on application.

While the present invention has been disclosed in connection with preferred embodiments thereof, it should be appreciated that there may be other embodiments of the present invention which fall within the spirit and scope of the present invention as defined by the appended claims.

What is claimed is:

1. A stable cosmetic emulsion of the oil-in-water type comprising an aqueous phase, an oily phase, and an emulsifier, wherein the oily phase comprises at least one silicone oil and the emulsifier is a polyoxyethylenated polyorganosiloxane with the following formula:

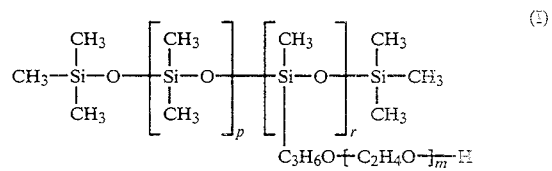

wherein:

p is a number between 15 and 35, r is a number between 2 and 6, m is a number between 5 and 15, and p, r, and m are such that the molecular weight ratio between the polyoxyethylenated side chain and the polysiloxane chain is approximately 50:50, the HLB of said emulsifier being between 9 and 12.

2. Emulsion according to claim 1, wherein p is a number between 20 and 30.

3. Emulsion according to claim 1, wherein m is a number between 8 and 12.

4. Emulsion according to claim 1, wherein the silicone oil is at least one member selected from the group consisting of volatile cyclic silicone oils and low-viscosity polydimethylsiloxanes.

5. Emulsion according to claim 1, wherein the polyoxyethylenated polyorganosiloxane with formula (I) has a molecular weight of between 2000 and 7000.

6. Emulsion according to claim 1, wherein the polyoxyethylenated polyorganosiloxane with formula (I) has a molecular weight of between 3500 and 4500.

7. Emulsion according to claim 1, wherein the polyoxyethylenated polyorganosiloxane has a molecular weight of 4000, an HLB of 10, and a molecular weight ratio between the polyoxyethylenated side chain and the polyorganosiloxane chain of 50:50.

8. Emulsion according to claim 1, wherein the proportion of the emulsifier is between 1 and 10 wt. % relative to the total weight of the emulsion.

9. Emulsion according to claim 1, wherein the proportion of the emulsifier is between 4 and 6 wt. % relative to the total weight of the emulsion.

10. Emulsion according to claim 1, wherein the aqueous phase of the emulsion represents 50 to 75 wt. % relative to the total weight of the emulsion.

11. Emulsion according to claim 1, wherein the aqueous phase of the emulsion represents 60 to 70 wt. % relative to the total weight of the emulsion.

12. Emulsion according to claim 1, wherein the oily phase of the emulsion represents 20 to 50 wt. % relative to the total weight of the emulsion.

13. Emulsion according to claim 1, wherein the oily phase of the emulsion represents 30 to 40 wt. % relative to the total weight of the emulsion.

14. Emulsion according to claim 1, wherein the oily phase contains silicone oil in a proportion greater than 50%.

15. Emulsion according to claim 1, wherein the oily phase contains silicone oil in a proportion between 70 and 100 wt. %.

16. Emulsion according to claim 1, wherein the emulsion additionally contains 0.05 to 20 wt. % of a gelling agent.

17. Emulsion according to claim 1, wherein the oily phase also contains dyes, sun filters, antioxidants, preservatives, and lipophilic active elements.

18. Emulsion according to claim 1, wherein the aqueous phase also contains dyes, preservatives, water-soluble surfactants, and hydrating agents.

19. Emulsion according to claim 1, wherein the oily phase consists essentially of said silicone oil.

20. A stable cosmetic emulsion of the oil-in-water type comprising an aqueous phase, an oily phase, and an emulsifier, wherein the oily phase comprises at least one silicone oil and the emulsifier is a polyoxyethylenated polyorganosiloxane having a molecular weight between 2,000 and 7,000 with the following formula:

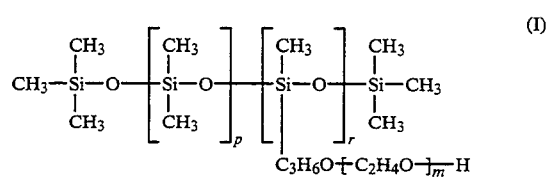

wherein:
p is a number between 15 and 35,
r is a number between 2 and 6,
m is a number between 5 and 15,
and p, r, and m are such that the molecular weight ratio between the polyoxyethylenated side chain and the polysiloxane chain is approximately 50:50,
the HLB of said emulsifier being between 9 and 12;
the proportion of the emulsifier being between 1 and 10 wt. % relative to the total weight of the emulsion;
the aqueous phase of the emulsion representing 50 to 75 wt. % relative to the total weight of the emulsion; and
the oily phase containing silicone oil in a proportion between 70 and 100 wt. %.

* * * * *